United States Patent [19]

Temple, Jr. et al.

[11] 4,206,307

[45] Jun. 3, 1980

[54] PREPARATION OF TETRAHYDROFOLIC ACID FROM FOLIC ACID

[75] Inventors: Carroll G. Temple, Jr.; Robert D. Elliott; Jerry D. Rose; John A. Montgomery, all of Birmingham, Ala.

[73] Assignee: United States of America, Washington, D.C.

[21] Appl. No.: 958,529

[22] Filed: Nov. 7, 1978

Related U.S. Application Data

[62] Division of Ser. No. 826,677, Aug. 22, 1977, Pat. No. 4,148,999.

[51] Int. Cl.$^2$ .......................................... C07D 475/04
[52] U.S. Cl. .................................................. 544/258
[58] Field of Search ........................................ 544/258

[56] References Cited

U.S. PATENT DOCUMENTS 2,741,608   4/1956   Shive ..................................... 544/258

Primary Examiner—Paul M. Coughlan, Jr.
Attorney, Agent, or Firm—Holman & Stern

[57] ABSTRACT

Improved methods for the preparation and purification of citrovorum factor are disclosed. The method includes improved procedures for hydrogenation of 10-formylfolic acid as well as for the reduction of folic acid. Also disclosed are improved procedures for opening of the imidazoline ring, and a non-chromatographic method for the purification of crude samples of citrovorum factor.

1 Claim, No Drawings

PREPARATION OF TETRAHYDROFOLIC ACID FROM FOLIC ACID

This is a divisional of application Ser. No. 826,677, filed Aug. 22, 1977, U.S. Pat. No. 4,148,899.

BACKGROUND AND SUMMARY OF THE INVENTION

The use of high-dose methotrexate therapy with citrovorum factor, 5-formyl-5,6,7,8-tetrahydrofolic acid, (5-CHO-THF) rescue is under active investigation for the treatment of a number of solid tumors and hematologic malignancies. The development of successful protocols will result in the need for larger amounts of citrovorum factor (5-CHO-THF).

By the present invention, there are provided improved methods for the preparation and purification of citrovorum factor. In one aspect of the invention, formylation of folic acid (FA) gave 10-CHO-FA, which was hydrogenated in trifluoroacetic acid to give high yields of (5, 10-CH-THF)+, the dehydration product of the initially formed 10-CHO-THF. In another aspect of the invention, the reduction of folic acid with borohydride followed by treatment of the resulting THF with formic acid gave good yields of (5, 10-CH-THF)+, isolated as the chloride. The effect of base concentration, temperature, and time of reaction on the conversion of (5, 10-CH-THF)+CL− to 5-CHO-THF was determined. These methods led to the preparation of the calcium salt dihydrate of 5-CHO-THF in high yields, which was about 78% pure. The identification of the impurities in these 5-CHO-THF samples was determined by high-pressure liquid chromatography, and the removal of the impurities was effected by Florisil chromatography. The discovery of a nonchromatographic method for the removal of most of the impurities from crude samples of 5-CHO-THF is also described.

The decrease in toxicity and increase in therapeutic benefit resulting from the adjuvant treatment of osteogenic sarcoma with a high dose of methotrexate followed by rescue with citrovorum factor, 5-formyl-5,6,7,8-tetrahydrofolic acid, (5-CHO-THF) has been established by Jaffe et al., *New Engl. J. Med.*, 291, 994 (1974). In this modality, 5-CHO-THF apparently protects normal sensitive tissue without canceling the inhibitory activity of methotrexate against neoplastic tissue. In addition, this form of therapy has been reported as being potentially effective against other malignancies, including refractory acute leukemia, bronchogenic carcinoma and head and neck cancer. Although the ultimate value in terms of cures of this form of therapy has not been fully documented, the development of the high-dose methotrexate regimen requires large amounts of both methotrexate and 5-CHO-THF. Recently, there has been reported by J. R. Piper and J. A. Montgomery, *J. Heterocycl. Chem.*, 11, 279 (1974), an improved method for the large-scale synthesis of methotrexate of high purity, and we now report improved procedures for the large-scale preparation and purification of 5-CHO-THF.

The synthesis and identification of 5-CHO-THF was carried out about 25 years ago, as described, for example, by Pohland et al., *J. Am. Chem. Soc.*, 73, 3247 (1951). In general, the adopted procedure involved the formylation of folic acid with formic acid, catalytic hydrogenation of the pyrazine ring of the resulting formic acid solution of 10-CHO-FA, and treatment of the product of the reduction with base at elevated temperatures to give crude 5-CHO-THF. In one procedure, bioassay of the crude product indicated that about a 22% yield of 5-CHO-THF was obtained. Purification was effected by column chromatography to give a low yield of 5-CHO-THF isolated as the barium salt pentahydrate. Although no yields were reported, a similar procedure was used for the preparation of the calcium salt of 5-CHO-THF.

In the prior art synthesis described above, it was recognized that 5-CHO-THF was dehydrated under acidic conditions to give (5, 10-CH-THF)+ and that the same product was formed from 10-CHO-THF resulting from the hydrogenation of 10-CHO-FA in formic acid. Treatment of (5, 10-CH-THF)+ with base at room temperature opened the imidazolinium ring to give mainly 10-CHO-THF (kinetic control), which underwent oxidation readily in the presence of oxygen and light to give decomposition products, as described by May et al., *J. Am. Chem. Soc.*, 73, 3067 (1951). In contrast, treatment of (5,10-CH-THF)+ with base at higher temperatures resulted in the formation of 5-CHO-THF (thermodynamic control) and decomposition products.

DESCRIPTION OF THE PREFERRED EMBODIMENTS

In the procedures according to the present invention, the first approach which was carried out included treatment of folic acid with 98% HCO$_2$H under N$_2$ at 60° to give 10-CHO-FA, which was purified by recrystallization from H$_2$O. All temperatures as stated herein are in degrees Centigrade. As was noted in the Pohland et al reference cited above, considerable difficulty was encountered in the hydrogenation of 10-CHO-FA in HCO$_2$H, with this reduction requiring more than 40 hr for the uptake of 2 molar equivalents of H$_2$ in the presence of platinum at room temperature and atmospheric pressure. Because of these results, conditions were sought for the reduction of 10-CHO-FA to give 10-CHO-THF, which might undergo in situ rearrangement to give 5-CHO-THF.

In the hydrogenation of 10-CHO-FA in pyridine in the presence of Pd, 2 molar equivalents of H$_2$ appeared to be absorbed within 5 hr; however, the recovery of 10-CHO-FA from this reaction indicated that hydrogenation of the solvent rather than the pyrazine ring of 10-CHO-FA had occurred. Based on the successful chemical reduction of folic acid to THF with Na$_2$S$_2$O$_4$, the reduction of 10-CHO-FA with this reagent was attempted. However, treatment of solutions of 10-CHO-FA in aqueous pyridine and in water at pH 6, 7, and 8.5 with Na$_2$S$_2$O$_4$ at 75° resulted in the formation of complex mixtures (TLC), which were not examined further. In addition, treatment of 10-CHO-FA either at room temperature with excess aqueous NaBH$_4$ (alkaline medium) or with refluxing aqueous NaBH$_3$CN at pH 6.7 resulted in extensive decomposition of the sample with little or no conversion to 5-CHO-THF. Although treatment of 10-CHO-FA with an equal weight of NaBH$_4$ while maintaining the pH of the medium near 8 with HOAc followed by refluxing the reaction mixture after adjustment to pH 6.7, as described hereinbelow, gave a mixture containing 5-CHO-THF, the mixture contained a large amount of unreduced 10-CHO-FA. These difficulties were circumvented by the catalytic hydrogenation of 10-CHO-FA in CF$_3$CO$_2$H containing prereduced PtO$_2$, which was more than 20 times faster than the hydrogenation of 10-CHO-FA in HCO$_2$H.

Next, the formylation and hydrogenation of folic acid without isolation of 10-CHO-FA was carried out. The solution of 10-CHO-FA in $HCO_2H$ resulting from the formylation of folic acid was diluted with an equal volume of $CF_3CO_2H$ and hydrogenated in the presence of prereduced $PtO_2$ (20% by weight of folic acid). The absorption of $H_2$ was slower than expected, and the reaction was repeated by removing the formic acid after formylation and using a smaller amount of catalyst, 5% by weight of folic acid. Under these conditions, the catalyst appeared to be poisoned after the uptake of 1 molar equivalent of $H_2$, but the reduction returned to the original rate after the addition of either freshly reduced $PtO_2$ (total 7.5% by weight of folic acid) or additional solvent. Based on these results, large-scale preparations were carried out by the formylation of folic acid with $HCO_2H$, recovering the $HCO_2H$ by distillation in vacuo, and hydrogenation of the resulting dried residue in $CF_3CO_2H$ containing prereduced $PtO_2$ (5% by weight of folic acid) at room temperature and atmospheric pressure. Although it was found that $CF_3CO_2H$ was reduced by Pt, the reaction was slower than the reduction of 10-CHO-FA. In addition, none of the reduction products from $CF_3CO_2H$ appeared to interfere either with the hydrogenation of 10-CHO-FA or the isolation of its reduction product. Both the solvent and catalyst could be recovered and reused at least five times.

Although the hydrogenation of 10-CHO-FA in $CF_3CO_2H$ probably gave 10-CHO-THF initially, this compound was readily dehydrated by the solvent. The resulting product was an acylated derivative (either formyl or trifluoroacetyl or both) of (5, 10-CH-THF)$^+$, isolated as a foam, which was converted by dissolution in 0.5 N HCl and concentration of the resulting solution to give a precipitate of practically pure (5, 10-CH-THF)$^+$ Cl$^-$. The obtainment of this product in an amount equal to the weight of the folic acid starting material indicated almost quantitative conversion in each step of the reaction sequence.

As a variation of the above approach, the large-scale reduction of folic acid to THF was investigated. Previously, the reduction of folic acid with borohydride gave a mixture of unreacted folic acid, DHF, and THF, the latter in yields up to 50%. Preliminary experiments indicated that an amount of sodium borohydride equal to the weight of folic acid was necessary to ensure complete reduction. To circumvent the use of a buffered medium, the reduction was carried out by the portionwise addition of an aqueous solution of $NaBH_4$ while maintaining the pH of the reaction medium near 8 by the addition of dilute HCl. However, some oxidation of the product occurred upon acidification of the reaction mixture to precipitate THF. Additional experiments revealed that the addition of HCl during the reduction was unnecessary as the system became buffered with borate at a pH of less than 10. The reoxidation of the THF during the isolation prevented by the addition of ascorbic acid during the acidification, which gave THF as a boron complex in 96% yield.

The direct conversion of the free acid of THF to 5-CHO-THF was effected with a refluxing 95:5 mixture of pyridine-$HCO_2H$ containing ascorbic acid. However, after a basic workup, the isolated CF contained a considerable amount of 10-CHO-DHF (TLC,HPLC), and no further work was carried out on this method.

Treatment of the THF product with either $HCO_2H$ or 2:1 $HCO_2H$-$CF_3CO_2H$ at room temperature gave mainly (5,10-CH-THF)$^+$. Similarly, the same product resulted from the condensation of THF with $(EtO)_3CH$ either in the presence of HCl at room temperature or in the presence of aqueous ascorbic acid at reflux. The yields and purity of the product appeared to be better in the procedures using $HCO_2H$, and the adopted procedure involved the dissolution of the precipitated THF directly in 98:2 $HCO_2H$-$CF_3CO_2H$, which provided (5,10-CH-THF)$^+$ free of boron impurities. This procedure was improved by elimination of the step involving the isolation of THF. Treatment of the aqueous solution (pH 7) of THF resulting from the $NaBH_4$ reduction of FA with an equal volume of $HCO_2H$ resulted in the isolation of a good yield of (5,10-CH-THF)$^+$CL$^-$.

On TLC many of these samples of (5,10-CH-THF)$^+$Cl$^-$ exhibited trace amounts of colored fluorescent impurities, which were removed by column chromatography. This imidazolinium chloride appeared to be stable in the solid state and in acidified aqueous solution, but, as noted above, was unstable in the presence of aqueous base. Additional information on the transformation of (5,10-CH-THF)$^+$Cl$^-$ in solutions was provided by the uv spectrum of the eluted peaks obtained on the chromatograms produced by high-pressure liquid reverse-phase chromatography.

When (5,10-CH-THF)$^+$Cl$^-$ was dissolved in pH 5 buffer, a mixture of 10-CHO-DHF, (5,10-CH-THF)$^+$, and 5-CHO-THF was formed. Presumably, (5,10-CH-THF)$^+$ was converted to 5,10-(HOCH)-THF, which underwent different modes of ring opening to give a small amount of 5-CHO-THF and a large amount of 10-CHO-THF followed by air oxidation of the latter to give 10-CHO-DHF. No 10-CHO-DHF was formed when (5,10-CH-THF)$^+$ was dissolved in pH 5 buffer containing ascorbic acid, the resulting solution exhibiting peaks only for (5,10-CH-THF)$^+$ and 5-CHO-THF. In contrast, the chromatogram of a solution of (5,10-CH-THF)$^+$ at pH 7 in the presence of ascorbic acid showed only a small amount of 10-CHO-DHF and two new peaks, which were tentatively assigned to 10-CHO-THF and 5,10-(HOCH)-THF. A later chromatogram of this solution showed that both of the peaks assigned to 10-CHO-THF and 5,10-(HOCH)-THF decreased with time while the 10-CHO-DHF peak increased even in the presence of ascorbic acid. The possibility was not eliminated from consideration that the peak assigned to 5,10-(HOCH)-THF was a tautomeric form of 10-CHO-DHF formed initially in the oxidation of 10-CHO-THF.

A solution of (5,10-CH-THF)$^+$Cl$^-$ at pH 13 containing ascorbic acid showed only the peak assigned to 10-CHO-THF. Although the uv spectrum of this peak was similar to that of 10-CHO-DHF, this resulted from 10-CHO-THF being converted rapidly to 10-CHO-DHF in the uv cell by uv radiation. This transformation was followed by measuring the increase in absorbance at a wavelength (330 nm) where 10-CHO-DHF gave a maximum after the peak was eluted from the column. Surprisingly, treatment of (5,10-CH-THF)$^+$Cl$^-$ with base at pH 11 with no protection from $O_2$ gave a high yield of 10-CHO-THF, which was isolated as its calcium salt. The structure of the latter was confirmed by its reconversion to (5,10-CH-THF)$^+$Cl$^-$ in an acidic medium (uv). Further treatment of 10-CHO-THF in a basic medium, however, resulted in the formation of a mixture of 10-CHO-DHF, 10-CHO-FA, and decomposition products. The obtainment of a purified sample of 10-CHO-DHF by elution of this mixture from a Florisil column with 0.1 M mercaptoethanol was unsuccessful because most of the sample decomposed on the column. Not only was the weight of the recovered material low (15%), but HPLC showed that the 10-CHO-DHF obtained was contaminated with p-aminobenzoylglutamic acid, pterins, and unidentified substances.

Previously, the (5,10-CH-THF)+ prepared in situ was converted to 5-CHO-THF in a hot, neutral or alkaline medium with a reaction time of about 1 hour. The solid (5,10-CH-THF)+Cl− prepared above was used in small-scale experiments to determine the effect of base concentration, temperature, and time of reaction on the purity of the 5-CHO-THF obtained. The progress of the reaction was followed by the determination of the uv spectrum of aliquot portions in 0.1 N NaOH and comparison of the $\lambda_{max}^{282}/\lambda_{min}^{242}$ ratio with that observed in the isolated sample of 5-CHO-THF. The uv data indicated that the ratio increased faster at the higher pH values, but also indicated that the ratio reached a maximum and then decreased. In addition, carrying out the reaction in a pressure apparatus at higher temperatures increased the rate of formation of citrovorum factor, but offered no advantage in regard to the purity of the product.

In one reaction in which the initial pH was 8.3 and the final pH 5.9, the same ratio was observed for the last aliquot portion and the isolated product suggesting that the reaction mixture was at equilibrium. In this reaction, a 75% increase in absorbancy at 282 nm occurred within 2.5 hours followed by a smaller increase over the remaining time of the experiment. A log A vs. time plot suggested that the conversion involved two sequential first-order reactions: possibly the transformation of (5,10-CH-THF)+ via 5,10-(HOCH)-THF to 5-CHO-THF and 10-CHO-THF followed by the reversible transformation of 10-CHO-THF via 5,10-(HOCH)-THF to 5-CHO-THF, a reaction that would be expected to predominate in the latter part of the conversion.

A highly significant result of this study was the discovery that the rate of opening of the imidazolinium ring of (5,10-CH-THF)+ was reasonable and that the purity of the 5-CHO-THF formed was greatest when the reaction was performed under neutral or slightly acidic conditions, at a pH of about 6.2 to 7.0. The latter result was confirmed in reactions with (5,10-CH-THF)+ at pH 11.4, 9, and 6.2 to give 5-CHO-THF of increasingly greater purity. However, experiments carried out in dilute solutions of 5-CHO-THF at 100° for 7 hours over the pH range 6.5–5.5 showed that increasing amounts of 10-CHO-DHF, 10-CHO-FA, and p-aminobenzoylglutamic acid (PABGA) were formed as the pH was decreased. For the large-scale synthesis of 5-CHO-THF from (5,10-CH-THF)+Cl− in concentrated solutions, the pH of the reaction medium was maintained near 6.7 for about 11 hours, which gave a product with a uv ratio of 3.4–3.9. These samples of 5-CHO-THF contained 10-CHO-DHF and PABGA as the major impurities and 10-CHO-FA and pterins as minor impurities. On TLC (5,10-CH-THF)+, 10-CHO-DHF, and 10-CHO-FA were detectable at less than 5% of the concentration of 5-CHO-THF. The major portion of the 10-CHO-DHF impurity in 5-CHO-THF samples was formed from unconverted (5,10-CH-THF)+ and 10-CHO-THF during the basic workup of the reaction.

The calcium salt of 5-CHO-THF appeared to have little or no solubility in anhydrous organic solvents; in fact, the salt was reprecipitated from an aqueous solution on the addition of DMAC. Also, recrystallization of the salt from a saturated solution of $CaCl_2$ and fractional precipitation of the salt from water-ethanol mixtures was unsatisfactory for the preparation of purified samples. In addition, the preparation of a purified sample of 5-CHO-THF by column chromatography was unsuccessful with the following packings: cation spherical resin developed with 0.1 M $CaCl_2$-$Ca(OH)_2$ (pH 10); cation exchange cellulose developed with 0.1 M $CaCl_2$-HCl (pH 5.5); Avicel cellulose developed with 0.1 M $CaCl_2$ (pH 8); silica gel H developed with 7:3 $H_2O$-acetone under water pressure; polyethylene powder developed with 3:1 $H_2O$-acetone; and Sephadex G-75 developed with $H_2O$ (pH 8). Practically pure 5-CHO-THF was obtained from crude samples by column chromatography on Sephadex G-10 developed with aqueous $Ca(OH)_2$ (pH 8), as further described hereinafter. A better method, however, was the column chromatography of crude samples on Florisil developed with aqueous mercaptoethanol, which gave 5-CHO-THF in 28–35% yield (from FA). These samples were shown by HPLC to contain only trace amounts of uv-absorbing impurities.

As a further aspect of the present invention, a non-chromatographic procedure was developed for the removal of most of the impurities from crude 5-CHO-THF samples. A solution of the sample in water containing magnesium chloride was adjusted to pH 12 with calcium hydroxide to produce a precipitate of the inorganic oxides, most of the impurities, and some 5-CHO-THF. From the filtrate 5-CHO-THF of good quality was recovered. This method is potentially the most convenient procedure for the purification of 5-CHO-THF.

The diagram shows the various reactions which take place in accordance with the present invention.

EXAMPLE 1

10-Formylfolic Acid (10-CHO-FA)

A mixture of FA.2H$_2$O (30.0 g. 62.8 mmol) and 98% HCO$_2$H (400 ml) was stirred under N$_2$ in a 60° oil bath for 2 hours. The resulting solution was evaporated to dryness under reduced pressure, and the residue was dried in vacuo over P$_2$O$_5$ and NaOH pellets for 18 hours to give a dry, glassy material: yield, 37.2 g. $\lambda_{max}$, nm: 0.1 N HCl-252, 322; pH 7-260, 349; 0.1 N NaOH-257, 365. Pmr (DMSO-d$_6$, 5.5% g/ml)- δ8.14 (CHO moiety, position unidentified), 8.63 (7-CH), 8.79 (10-CHO). TLC [Avicel, 0.1 M phosphate buffer (pH 7)]-Rf~0.85 (fluorescent).

In a 1.0-g run the isolated residue was recrystallized from hot H$_2$O (110 ml) to give the monohydrate: yield, 0.57 g (56%). This sample underwent decomposition from about 200°. $\lambda_{max}$, nm ($\epsilon \times 10^{-3}$): 0.1 N HCl-252 (26.5), 322 (8.69); pH 7-249 sh (24.3), 263 br (25.6), 348 (6.15), 357 sh (5.81); 0.1 N NaOH-257 (39.0), 367 (7.62). $\nu_{max}$, cm$^{-1}$: 1680 br. Pmr (DMSO-d$_6$, 4.3% g/ml)- δ8.63 (7-CH), 8.79 (10-CHO).

DIAGRAM

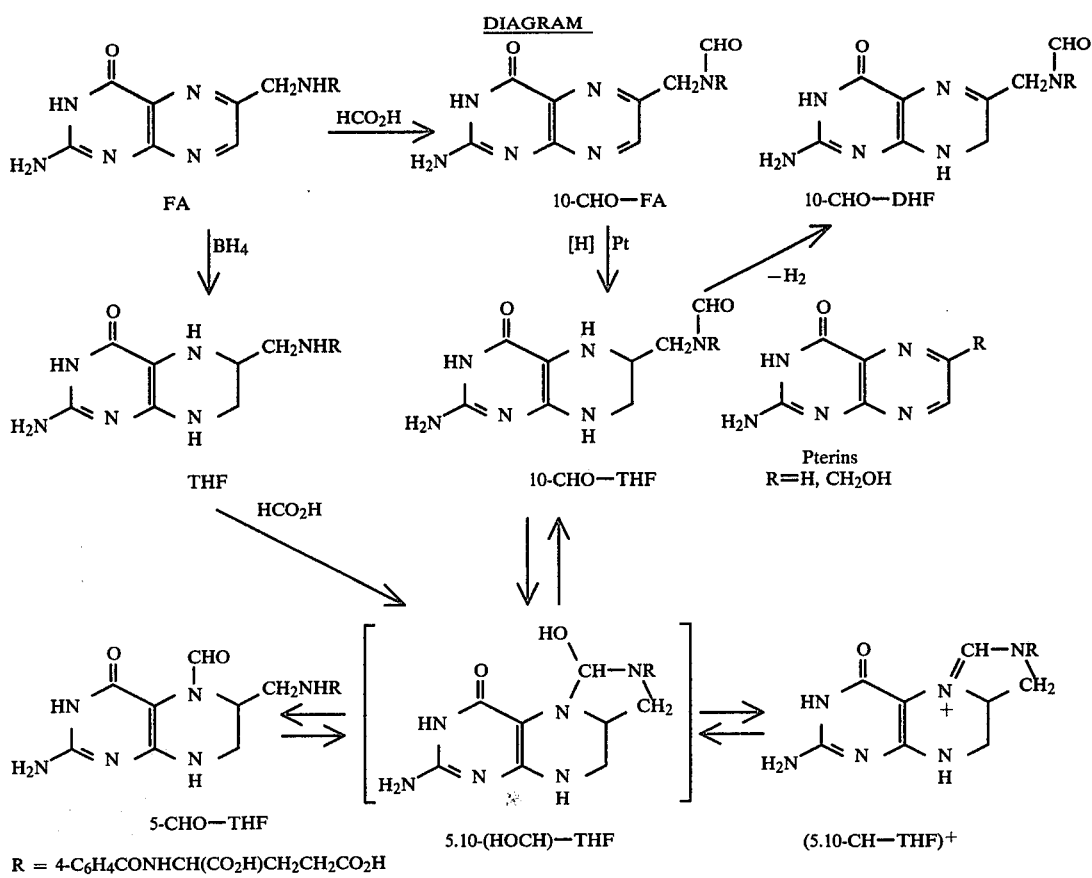

R = 4-C₆H₄CONHCH(CO₂H)CH₂CH₂CO₂H

Anal. Calcd for $C_{20}H_{19}N_7O_7 \cdot H_2O$: C, 49.28; H, 4.34; N, 20.12. Found: C, 49.12; H, 4.27; N, 19.97.

EXAMPLE 2

Calcium 10-Formyl-7,8-dihydrofolate

A suspension of (5,10-CH-THF)⁺Cl⁻ (10.0 g) in H₂O (315 ml) was stirred and treated with 1 N NaOH (~85 ml) to give a clear yellow solution (pH 11, meter). After stirring at room temperature with free access to air for 2 hours, the solution was adjusted to pH 7.5 with dilute HCl followed by the addition of a clarified solution of CaCl₂ (2.5 g/5 ml) and EtOH (150 ml). The yellow precipitate (0.6 g) that deposited was removed by filtration, and the filtrate was diluted with an additional amount of EtOH (800 ml). The resulting pale yellow precipitate was collected by filtration and dried in vacuo over P₂O₅: yield, 9.74 g. The uv spectrum indicated that this solid was mainly calcium 10-formyl-5,6,7,8-tetrahydrofolate. $\lambda_{max}$, nm ($\epsilon \times 10^{-3}$): pH 7 (1% mercaptoethanol)-257 (18.8), 305 sh (6.12), 340 sh (2.85). After 24 hours this solution gave the following spectrum: 262 (17.5), 305 sh (7.56), 340 sh (3.60).

Anal. Calcd for $C_{20}H_{21}N_7O_7 \cdot Ca \cdot 0.75 C_2H_6O \cdot 2H_2O$: C, 44.36; H, 5.11; N, 16.84; Ca, 6.89; Ash (CaO), 9.65. Found: C, 44.69; H, 4.91; N, 17.06; Ca, 6.82; Ash (CaO), 10.17.

A portion of the above solid (5.0 g) was dissolved in H₂O (500 ml), and the solution (pH 7.4) was stirred in the presence of air at room temperature for 18 hours. During this period, a yellow solid deposited as the pH of the solution dropped to 6.7. The solid was collected by filtration and dried in vacuo over P₂O₅: yield, 0.76 g. The ¹H NMR spectrum, elemental analyses, and HPLC assay of this sample showed that it was a 2:1 mixture of the calcium salts of 10-formyl-7,8-dihydrofolate and 10-formylfolic acid. $\lambda_{max}$, nm ($\epsilon \times 10^{-3}$): pH 7—233 (30.8), 260 sh (22.8), 266 sh (22.3), 335 (6.68). TLC [Avicel, 0.1 M phosphate buffer pH 7)]—$R_f$0.70 (10-CHO-DHF), 0.86 (10-CHO-FA) (both fluorescent).

Anal. Calcd for $(C_{20}H_{19}N_7O_7)_2(C_{20}H_{17}N_7O_7) \cdot Ca \cdot 2H_2O$: C, 44.09; H, 4.13; N, 18.00; Ca, 7.36; Ash (CaO), 10.30. Found: C, 44.18; H, 4.10; N, 17.99; Ca, 7.33; Ash (CaO), 9.93.

Dilution of the filtrate from the above solid with EtOH gave a mixture of the salts of 10-formyl-7,8-dihydro- and 10-formylfolic acids (3.21 g) that was contaminated with other impurities (p-aminobenzoylglutamic acid, pterins).

EXAMPLE 3

5,6,7,8-Tetrahydrofolic Acid

To a suspension of folic acid dihydrate (47.8 g, 100 mmol) in deaerated H₂O (1,000 ml), which was cooled in an ice bath, was added slowly with stirring 50% NaOH (10.5 ml). The resulting dark yellow solution (pH 8.0, meter) was treated over a 10-min period with a solution of NaBH₄ (58 g) in H₂O (150 ml). The solution was stirred for an additional 30 min, the pH increasing during this period from 8.4 to 8.8. Excess NaBH₄ was decomposed by the addition of 6 N HCl (caution, vigorous effervescence) until the pH of the solution was 6.8. Solid ascorbic acid (5 g) was added and stirring continued until complete dissolution occurred. The resulting solution was adjusted to pH 3.7 with 6 N HCl (total volume, 165 ml). The cream-colored precipitate was collected by filtration under $N_2$, washed with ice cold HCl (pH 3.5, 200 ml) containing ascorbic acid (2 g) and dried to constant weight in vacuo over $P_2O_5$ at room temperature: yield, 60.0 g (96%). Solutions for the uv spectra determinations were obtained by dissolution of tetrahydrofolic acid (5.5 mg) by the successive addition of mercaptoethanol (2.5 ml) and water (22.5 ml) and dilution of the resulting stock solution with the appropriate solvent (5→50 ml). $\lambda_{max}$, nm ($\epsilon \times 10^{-3}$): 0.1 N HCl—270 (23.5), 292 (20.8); pH 7—297 (25.7); 0.1 N NaOH—297 (25.9). TLC [DEAE cellulose; 0.005 M $KH_2PO_4$+0.5 M NaCl+0.2 M mercaptoethanol (pH 7)]—$R_f$~0.44 (elongated).

This sample analyzed for the following composition: Anal. Calcd for $C_{19}H_{23}N_7O_6 \cdot 1.66HCl \cdot 1.68H_3BO_3 \cdot 0.74H_2O$: C, 36.66; H, 5.04; B, 2.92; Cl, 9.45; N, 15.75. Found: C, 36.69; H, 5.20; B, 2.89; Cl, 9.45; N, 15.66.

EXAMPLE 4

Calcium Salt of Citrovorum Factor

The combined crops of (5,10-CH-THF)+Cl− (1212 g), prepared as described below, were added with stirring under a $N_2$ atmosphere to boiling $H_2O$ (30 l.) over a period of 20 minutes. During the addition and thereafter for 1 hour, hot, oxygen-free 3.7 N NaOH (~21.) was added at a rate to maintain an acidic reaction medium. At this point, complete dissolution of the solid was obtained with oxygen-free 1 N NaOH. The resulting solution was refluxed for 11 hours while maintaining the pH between 6.5–6.9 (meter) with 1 N NaOH (total, ~450 ml). The progress of the reaction was followed by determining the HPLC chromatograms of aliquot portions. After standing for an additional 8 hours without heat, the solution (56°, pH 7.7) was treated with a clarified solution (1200 ml) of $CaCl_2$ (600 g), which lowered the pH to 7.2. The solution was diluted with EtOH (3.2 l.) and transferred through tygon tubing with a peristaltic pump to a flask cooled in an ice-salt mixture. When the temperature of the mixture was less than 10°, the bright yellow solid that deposited was removed by filtration. On exposure to air, this solid darkened to a brown color and became gummy. TLC of the semidried residue (~400 g) showed that it contained 5-CHO-THF contaminated with numerous impurities. Further work on the characterization of this residue is described in the section of the nonchromatographic purification of 5-CHO-THF.

The clear yellow filtrate from above was pumped into a large container and diluted with EtOH (total, 102 l.). The resulting slurry of cream-colored precipitate of 5-CHO-THF.Ca was cooled (<10°) in an ice bath for 18 hours, the solid was collected by filtration, washed with EtOH (7 l.), and dried in vacuo over $P_2O_5$: yield, 897 g (~45% from FA). $\lambda_{max}$, nm ($\epsilon \times 10^{-3}$): 0.1 N NaOH—282 (28.8) [$\lambda_{max}^{282}/\lambda_{min}^{242}$ (0.1 N NaOH), 3.6]. TLC [Avicel, 0.1 M phosphate buffer (pH 7)]—$R_f$ 0.76 (10-CHO-DHF), 0.85 (CF, absorbing), 0.93 (10-CHO-FA).

Anal. Calcd for $C_{20}H_{21}N_7C_7 \cdot Ca \cdot 0.5C_2H_6O \cdot 1.8H_2O$: C, 44.49; H, 4.91; N, 17.29; Ca, 7.07; Ash (CaO), 9.89. Found: C, 44.49; H, 4.97; N, 17.29; Ca, 7.18; Ash (CaO), 9.65.

HPLC assay of this sample indicated the presence of 5-CHO-THF.Ca (78%) and, excluding ethanol and water, the following impurities: PABGA.Ca (3.1%), 10-CHO-DHF (4.6%), 10-CHO-FA (<0.5%), pterins (1.0%), and unidentified and undetected material (3.0%).

EXAMPLE 5

5,10-Methenyl-5,6,7,8-tetrahydrofolic Acid (5,10-CH-THF)+(A).

A suspension of $PtO_2$ (1.50 g) in $CF_3CO_2H$ (600 ml) was hydrogenated at 24° and atmospheric pressure until the theoretical volume (322 ml) of $H_2$ was absorbed (<5 min). To this mixture was added a solution of crude 10-CHO-FA (37.1 g, from 30 g FA) in $CF_3CO_2H$ (900 ml), and the whole was hydrogenated with rapid magnetic stirring at 24.5° and atmospheric pressure. Within 2.5 hours, the theoretical amount of $H_2$ was absorbed (3,095 ml). The resulting mixture was filtered (Celite) under $N_2$ pressure, and the filtrate was evaporated at less than 40° under reduced pressure to give a dry, porous foam. After drying this sample for 18 hours over $P_2O_5$, the foam was dissolved in 0.5 M HCl (200 ml) that was 0.1 M in 2-mercaptoethanol. The dark solution was warmed to 40° ($H_2O$ bath), treated with charcoal (0.5 g), and filtered (Celite). The filter pad was washed with the 0.5 M HCl-0.1 M mercaptoethanol solvent (100 ml), and the clear yellow filtrate was concentrated at 40° to ⅔ volume under aspirator vacuum. The resulting mixture was cooled; the yellow solid of the chloride salt was collected by filtration, washed with the 0.5 M HCl-0.01 M mercaptoethanol solvent (25 ml), and dried in vacuo over $P_2O_5$ and NaOH pellets for 18 hours: yield, 29.9 g. $\lambda_{max}$, nm: 1 N HCl—286, 347 ($A_{max}^{347}/A_{min}^{302}$=2.60; lit. $A_{max}^{348}/A_{min}^{305}$=2.46). $\nu_{max}$, cm$^{-1}$: 1730, 1655 sh, 1630, 1620 sh. Pmr ($CF_3CO_2D$, 5.3% g/ml), δ9.57 (methenyl CH). TLC [Avicel, 0.1 M phosphate buffer (pH 7)] showed an elongated bluish-white fluorescent spot at $R_f$ 0.47 and a yellow fluorescent impurity spot near the origin. Concentration of the filtrate to about 20 ml from the first crop gave a dark colored solid: yield, 0.9 g. TLC indicated that this sample contained more of the yellow fluorescent impurity. In this hydrogenation both the catalyst and solvent could be recovered and reused at least 5 times.

The yellow fluorescent impurity in crude (5,10-CH-THF)+Cl− from another run was removed by column chromatography. This sample (0.50 g) was eluted at a rate of 6 ml/10 min from an Avicel (75 g) column with HCl (pH 2.3) that was 0.01 M in 2-mercaptoethanol. Fractions 20–25, which contained crystalline (5,10-CH-THF)+Cl−, were combined and concentrated in vacuo below room temperature to a thick slurry. The yellow solid was collected by filtration under $N_2$, washed with EtOH and $Et_2O$, and dried in vacuo over $P_2O_5$ for 18 hours: yield, 0.24 g (48% recovery). $\lambda_{max}$, nm ($\epsilon \times 10^{-3}$): 1 N HCl—286 (12.4), 347 (25.8) [$A_{max}^{347}/A_{min}^{303}$=2.57]. $\nu_{max}$, cm$^{-1}$: 1730, 1660 sh, 1630 br. Pmr ($CF_3CO_2D$, 5.3% g/ml), 9.56 (methenyl CH). TLC [DEAE cellulose; 0.005 M phosphate buffer, 0.5 M NaCl, 0.2 M mercaptoethanol (pH 7)] showed one major spot and a trace amount of a lower absorbing impurity spot.

Anal. Calcd for $C_{20}H_{22}ClN_7O_6 \cdot 0.1HCl \cdot H_2O$: C, 46.78; H, 4.73; Cl, 7.59; N, 19.09. Found: C, 46.87; H, 4.79; Cl, 7.50; N, 18.99.

Fractions 26–42 from the above column were treated in the same manner: yield, 0.14 g (28% recovery). $\lambda_{max}$, nm: 1 N HCl—286, 347 [$A_{max}^{347}/A_{min}^{303}$=2.62]. TLC of this sample was similar to the first crop. The total amount recovered was 0.38 g (76%).

In another run a sample of crude (5,10-CH-THF)+Cl− (100 mg) was eluted at a rate of 4 drops/min from an Avicel (15 g) column (1×55 cm) with 0.1 M $HCO_2H$-0.01 M mercaptoethanol. Twelve fractions (5 ml each) were collected in which fractions 5–7 deposited crystalline product. These fractions were combined and cooled; the solid was collected by filtration, washed with 0.1 M $HCO_2H$-0.01 M mercaptoethanol, and dried in vacuo over $P_2O_5$: yield, 12 mg (12% recovery). This material was homogeneous on TLC (DEAE cellulose). The mother liquor from this sample and fractions 4 and 8–12 were combined and evaporated to dryness. The resulting residue (70 mg) was recrystallized from 0.1 M $HCO_2H$-0.01 M mercaptoethanol: yield, 35 mg (35% recovery). $\lambda_{max}$, nm ($\epsilon \times 10^{-3}$): 1 N HCl—286 (12.1), 347 (25.5) [$A_{max}^{347}/A_{min}^{303}=2.60$]. This material was homogeneous on TLC; however, elemental analyses indicated that this material was a mixture of the chloride (34%) and the corresponding meso-ionic compound (66%).

Anal. Calcd for [34% [($C_{20}H_{22}N_7O_6$)+Cl−],66% ($C_{20}H_{21}N_7O_6$)].3$H_2O$: C, 46.03; H, 5.28; Cl, 2.31; N, 18.79. Found: C, 46.00; H, 5.20; Cl, 2.37; N, 18.57.

(B) To a suspension of FA.2$H_2O$ (1673 g, 3.500 mol) in $H_2O$ (35 l.), which was under an atmosphere of $N_2$ and cooled to 8° in an ice bath, was added slowly with stirring 50% NaOH (370 ml). The resulting clear yellow solution (pH 8, meter) was treated over a one-hour period with a solution of $NaBH_4$ (1673 g) in $H_2O$ (5 l.). During the addition, the temperature increased to a maximum of 17°. The solution was stirred for an additional 30 minutes, followed by the decomposition of excess $NaBH_4$ with concd HCl. The large amount of $H_2$ generated was vented to a hood. During the first half of the decomposition step, efficient cooling was required to maintain the temperature of the solution below 24°. The decomposition of $NaBH_4$ was essentially complete after the addition of 2000 ml of concd HCl, which required a period of 3 hours. The resulting solution (pH 8.3) was adjusted to pH 6.6 with 500 ml of concd HCl over a period of 30 minutes. At this point, a solution of ascorbic acid (175 g) in $H_2O$ (800 ml) was added to protect THF against air oxidation. The pH of the solution was then adjusted to 3.5 with an additional 1800 ml of concentrated HCl over a period of one hour. The resulting cream-colored suspension of THF was pumped into a Buchner funnel (11-l. capacity) fitted with a glass fiber paper (Whatman GF/D) and under an atmosphere of $N_2$. This filtration (aspirator pressure) was carried out in two batches because of the large amount of solid. Near the end of the filtration, a small portion (~50 g) of the THF slurry was exposed to air and was discarded. Each batch of the wet precipitate was dissolved in a mixture of 98:2 $HCO_2H$ (97%)-$CF_3CO_2H$ and transferred under aspirated vacuum to a 24-l. flask. A total volume of 12,750 ml of the acid mixture was used. After standing at room temperature for 14 hours, the dark red solution was evaporated to dryness in vacuo at a maximum $H_2O$-bath temperature of 60°. The superficially dried residue was suspended in 0.5 N HCl (35 l.) containing 2-mercaptoethanol (1 ml/l. of acid), warmed to 45°, and the whole was concentrated under aspirator pressure to remove formic and trifluoroacetic acids (~3 l.). After standing at room temperature for 18 hours, the (5,10-CH-THF)+Cl− was collected by filtration on a glass fiber paper, washed with 0.01 N HCl (6 l.), and dried in vacuo over $P_2O_5$: yield, 1119 g (63%). A boron analysis indicated the absence of boron salts.

Anal. Calcd for ($C_{20}H_{22}N_7O_6$)+Cl−.$H_2O$: C, 47.11; H, 4.74; Cl, 6.75; N, 19.23. Found: C, 47.24; H, 4.65; Cl, 7.16; N, 19.28.

Concentration of the filtrate to about one-third the original volume deposited a second crop, which was less pure (5,10-CH-THF)+Cl−: yield, 95 g (~5%). The total yield was 1214 g (~68%).

Modification of the procedure described above gave a higher yield of (5,10-CH-THF)+Cl−. FA.2$H_2O$ (10.0 g, 20.9 mmol) was treated with $NaBH_4$, the excess $NaBH_4$ was decomposed, and the resulting solution (pH 7) was diluted with 95% $HCO_2H$ (270 ml). During the addition of $HCO_2H$, a precipitate of 5,6,7,8-tetrahydrofolic acid was formed, which redissolved rapidly as the volume of $HCO_2H$ increased (final pH, 1.1). After standing for 18 hours at room temperature, an inorganic precipitate (5.6 g) was removed by filtration. The filtrate was treated with concentrated HCl (3.5 ml) and evaporated to dryness under reduced pressure at 40°. The resulting solid was washed by stirring with cold 1% ascorbic acid (100 ml), collected by filtration, washed with additional 1% ascorbic acid solution, and dried in vacuo over $P_2O_5$: yield, 10.0 g. A boron analysis indicated that this sample contained boron.

Anal. Calcd for $C_{20}H_{22}ClN_7O_6$.0.3$H_3BO_3$.2$H_2O$: C, 43.96; H, 4.96; B, 0.59; Cl, 6.49; N, 14.94. Found: C, 43.78; H, 4.89; B, 0.61; Cl, 6.59; N, 17.70.

The above solid was stirred for one hour in cold 0.5 N HCl (100 ml) containing mercaptoethanol (0.1 ml), recollected by filtration under $N_2$ pressure, washed in the funnel with additional 0.01 N HCl (100 ml), and dried in vacuo over $P_2O_5$: yield, 8.4 g (79%). A boron analysis indicated that this sample contained a trace amount of a boron impurity (found, 0.06%).

Anal. Calcd for $C_{20}H_{22}ClN_7O_6$.$H_2O$: C, 47.11; H, 4.74; Cl, 6.95; N, 19.23. Found: C, 47.34; H, 4.73; Cl, 6.84; N, 19.29.

(C) A solution of THF.1.66HCl.0.74$H_2O$.1.68$H_3BO$ (2.4 g, 3.9 mmol) in a 1:2 mixture of $H_2O$-(EtO)$_3$CH (60 ml) containing ascorbic acid (0.25 g) was refluxed for five hours and allowed to stand at room temperature for 18 hours. The resulting mixture was diluted with (EtO)$_3$CH, and the solid was collected by filtration, washed with $Et_2O$, and dried in vacuo over $P_2O_5$ to give crude (5,10-CH-THF)+Cl−: yield, 1.5 g. TLC (Avicel, 0.1 M phosphate, pH 7) showed that the product was contaminated with fluorescent impurities and ascorbic acid.

EXAMPLE 6

Purification of 5-CHO-THF (Citrovorum Factor)

(A) Sephadex G-10 Column Chromatography

A glass column (5×118 cm) was poured in one portion with Sephadex G-10 (825 g) in $H_2O$ and packed to a height of 108 cm with $H_2O$ adjusted to pH 8 (meter) with CaO. A solution of impure 5-CHO-THF.Ca (9.0 g) in aqueous Ca(OH)$_2$ (pH 8) (40 ml) was applied to the column over a period of four hours, and the resulting column was developed with the same solvent at a rate of about 16 ml/hour (unless otherwise noted). After about 48 hours, a mixture of 10-CHO-FA and 10-CHO-DHF, which trailed back into the band containing 5-CHO-THF, was eluted. The front of the band containing 5-CHO-THF was visibly yellow. Fractions were taken every 30 minutes, and the presence of 5-CHO- THF in a fraction was determined by TLC on Avicel plates (0.1 M NaH$_2$PO$_4$, pH 7). The combined fractions were adjusted to about pH 7.5 with aqueous Ca(OH)$_2$ and diluted with EtOH to the point of cloudiness. After cooling in an ice bath (unless otherwise noted), the first crop was collected by filtration under N$_2$. A second crop was obtained from the filtrate by the addition of 5 volumes of EtOH. The first experiment involved three column runs, the results of which are summarized in Table 1. On alternate weeks, a second sample of 5-CHO-THF was chromatographed on the same column, the results of which are also shown in Table 1.

The results in Table 1 indicated that p-aminobenzoyltion of 10-CHO-DHF is found in the (A) samples, indicating that the solubility of the Ca salt of 10-CHO-DHF is less than the Ca salt of 5-CHO-THF.

One sample (0.82 g) in Table 1 (run I, column 3) was retained. The last 3 samples from both run I, column 3, and run II, column 2, were combined, and the composite sample (6.3 g) was dissolved in H$_2$O (125 ml). This solution was adjusted to pH 7.5 (meter) with aqueous Ca(OH)$_2$ and diluted with EtOH (~15 ml) to give a slightly cloudy solution containing a small amount of trash. During the filtration (under N$_2$) of this mixture under aspirator pressure, a yellowish precipitate began to deposit from the unfiltered portion.

Table 1[m]

| Experiment | Number of fractions (30 min. each) combined (vol., ml) | Wt.[b] Recovered (g) | $A^{282}/A^{242c}$ max min | PABGA | 10-CHO—FA and (5.10-CH—THF)$^+$ | 10-CHO—DHF | 5-CHO—THF |
|---|---|---|---|---|---|---|---|
| Crude 5-CHO—THF | — | — | 3.43 | <3 | <1 | <10 | ~86 |
| Run I, Col. 1 | 8 (120) | A. 2.04[e] | 3.04 | 1.3 | 2.7 | <25.6 | ~72 |
| Crude 5-CHO—THF (9 g) in 40 ml of solvent | | B. 1.51 | 3.94 | <1 | <1 | <8.5 | ~90 |
| | 16 (240) | A. 1.79 | 3.99 | 2 | trace | <6.4 | ~92 |
| | | B. 1.98 | 4.59 | 2 | trace | <2.5 | ~95 |
| | | total 7.32 (81%) | | | | | |
| Run 1. Col. 2 | 11 (105) | A. 109[f] | 3.46 | trace | 2.3 | <10.4 | ~87 |
| 3-CHO—THF (6.4 g) from Col. 1 in 30 ml of solvent | | B. 1.24 | 4.31 | trace | <1.0 | <4.0 | ~95 |
| | 9 (86) | A. 0.56 | 4.26 | trace | <1.0 | <5.4 | ~94 |
| | | B. 0.95 | 4.52 | 2.4 | — | <2.3 | ~95 |
| | 15 (143) | A. 0.90 | 4.40 | trace | <1.0 | <2.2 | ~97 |
| | | B. 0.75 | 4.61 | 1 | — | <1 | ~98 |
| | | total 5.48 (86%) | | | | | |
| Run 1. Col. 3 | 10 (78) | A. 0.08[g] | 4.22 | trace | <1 | <6.5 | ~92 |
| 5-CHO—THF (4.2 g) from Col. 2 in 20 ml of solvent | | B. 0.82 | 4.59 | trace | — | <3.8 | ~96 |
| | 18 (140) | A. 0.08[g] | 4.54 | trace | — | <2.5 | ~97 |
| | | B. 2.04 | 4.58 | 1 | — | <1.3 | ~98 |
| | 4 (32) | A. —[g] | — | — | — | — | — |
| | | B. 0.21 | 4.73 | — | — | <1 | ~99 |
| | 3 (24) | A. —[g] | — | — | — | — | — |
| | | B. 0.18 | 4.69 | — | — | <1 | ~99 |
| | | total 2.40 (81%)/~99 | | | | | |
| | | total 2.40 (8190) | | | | | |
| Run B. Col. 1 | 12 (94) | A. 1.45[h] | 3.43 | <1 | 1.7 | <17.6 | ~80 |
| Crude 5-CHO—THF (9 g) in 40 ml of solvent | | B. 2.18 | 4.14 | <1 | <1 | <7 | ~91 |
| | 12 (94) | A. 1.13 | 4.16 | 1.1 | — | <5.4 | ~93 |
| | | B. 1.09 | 4.50 | 8.0 | — | <1.6 | ~90 |
| | 10 (78) | A. 0.41 | 4.65 | <1 | — | <3 | ~96 |
| | | B. 0.67 | 4.54 | 2.2 | — | <1 | ~97 |
| | | total 6.93 (77%) | | | | | |
| Run B. Col. 2 | 7 (53) | A. 0.01[g] | — | trace | 3.4 | <22 | ~75 |
| 5-CHO—THF (5.4 g) in 25 ml of solvent | | B. 0.53 | 4.04 | trace | 1.1 | <9.4 | ~89 |
| | 14 (105) | A. 0.17[g] | 4.35 | trace | <1 | <5.6 | ~93 |
| | | B. 1.63 | 4.61 | <1 | — | <3.1 | ~96 |
| | 26 (195) | A. 0.32[g] | 4.44 | <1 | <1 | <2.5 | ~95 |
| | | B. 1.99 | 4.52 | 4.3 | — | <1.3 | ~94 |
| | | total 4.67 (80%) | | | | | |

[a]The Sephadex G-10 column was washed with aqueous Ca(OH), (5.000 ml) between each run.
[b]A refers to the first crop, B to the second crop.
[c]Determined in 0.1 N NaOH, Lederle's 5-CHO—THF, ratio 4.86.
[d]Amount of impurities estimated by HPLC, 5-CHO—THF determined by difference and does not take into account the percent of solvates and calcium. Also, small peaks of unidentified substances are observed.
[e]Reprecipitated from H$_2$O with EtOH to give 1.1 g (ratio - 3.36), which was included in sample used for column 2.
[f]Excluded from column 3.
[g]The cooled mixture was allowed to rewarm to room temperature, which redissolved most of the precipitate.
[h]Excluded from column 3, run 11.

glutamic acid is eluted toward the end of the band containing 5-CHO-THF. Also, this impurity is concentrated in the (B) samples, which were obtained by intentionally diluting the filtrate with a large volume of EtOH to recover as much weight as possible. In addition, the results indicated that elution of most of 10-CHO-FA and 10-CHO-DHF occurred near the front of the band containing 5-CHO-THF. A greater concentra- The solid was collected by filtration and dried in vacuo over P$_2$O$_5$: yield, 0.70 g (11% recovery). TLC (Avicel, 0.1 M NaH$_2$PO$_4$, pH 7) showed that this sample was mainly 5-CHO-THF contaminated with 10-CHO-DHF, 5,10-CH-THF)$^+$, and a yellow fluorescent impurity near the origin. HPLC indicated the presence of PABGA (<1%), 10-CHO-DHF (<2.9%), (5,10-CH- THF)+ (<1%), and 5-CHO-THF (95.1% by difference). $\lambda_{max}^{282}/\lambda_{min}^{242} = 4.50$.

The filtrate was diluted with additional EtOH (total, 250 ml), and the white precipitate was collected by filtration under $N_2$: yield, 4.8 g (76% recovery). TLC showed that the sample contained trace amounts of 10-CHO-DHF and a yellow fluorescent impurity near the origin. HPLC indicated the presence of PABGA (<1%), 10-CHO-DHF (<1%), and 5-CHO-THF (~98% by difference). $\lambda_{max}$, nm ($\epsilon \times 10^{-3}$): pH 7-286 (30.4); 0.1 N NaOH-282 (29.7). $\lambda_{max}^{282}/\lambda_{min}^{242} = 4.67$.

Anal. Calcd for $C_{20}H_{21}N_7O_7 \cdot 2H_2O \cdot Ca$: C, 43.87; H, 4.60; N, 17.91; Ca, 7.32; Ash (CaO), 10.24. Found: C, 43.91; H, 4.63; N, 17.80; Ca, 7.10; Ash (CaO), 10.64.

The filtrate from the above sample was diluted with additional EtOH (total, 625 ml), and the white solid was collected by filtration under $N_2$: yield, 0.32 g (5% recovery). TLC showed only 5-CHO-THF. HPLC indicated the presence of PABGA (4.3%) and 5-CHO-THF (95.7% by difference). $\lambda_{max}^{282}/\lambda_{min}^{242} = 4.65$.

The total amount recovered was 5.8 g (92%).

Purified samples of the calcium salt of 5-CHO-THF gave a $\lambda_{max}^{282}/\lambda_{min}^{242}$ value between 4.6–5.4, probably because a slight change in the minimum resulted in a large change in the ratio.

(B) Florisil Chromatography

Florisil (350 g, 100-200 mesh) was suspended in $H_2O$ (3 times), and the fines were removed by decantation. The defined slurry of florisil was poured into a glass column (3.8×67 cm) and washed with $H_2O$ until the effluent was clear and then with 0.2% aqueous mercaptoethanol (4000 ml). After a solution of impure 5-CHO-THF (3.0 g) in 0.2% aqueous mercaptoethanol (10 ml) was applied, the column was developed with 0.2% aqueous mercaptoethanol at a rate of 0.3 ml/min. The progress of the development was followed by a uv monitor. After 17.5 hours a uv-absorbing material, probably p-aminobenzoylglutamic acid, was eluted from the column over the next 8 hours. At this time (25.5 hours), 5-CHO-THF began to elute and four fractions were collected (see Table 2).

In earlier work on florisil chromatography of crude 5-CHO-THF samples at a faster flow rate, the blue fluorescent spots above and below 5-CHO-THF (TLC) were eluted before and during the elution of 5-CHO-THF rather than after 5-CHO-THF as described above. Although florisil might have better absorbent characteristics for 10-CHO-FA and 10-CHO-DHF at the slower rate, other work suggested that under these conditions the basic nature of the mobile phase (pH ~8.5) resulted in the decomposition of these impurities.

The same from fraction 1 appeared to contain a water-insoluble material and was reprecipitated from an aqueous solution with EtOH: yield, 0.29 g (6.5% from FA); $\lambda_{max}^{282}/\lambda_{min}^{242} = 4.37$. HPLC indicated that this sample contained only trace amounts of uv-absorbing impurities.

Anal. Calcd for $C_{20}H_{21}N_7O_7 \cdot 3.8H_2O \cdot Ca$: C, 41.42; H, 4.97; N, 16.91; Ca, 6.91; Ash (CaO), 9.67. Found: C, 41.36; H, 4.91; N, 16.74; Ca, 7.04; Ash (CaO), 9.78.

The sample from fraction 2 (1.2 g, 27% from FA) contained only trace amounts of uv-absorbing impurities (HPLC) and was analyzed without further purification.

Anal. Calcd for $C_{20}H_{21}N_7O_7 \cdot 3.5H_2O \cdot Ca$: C, 41.81; H, 4.91; N, 17.07; Ca, 6.98; Ash (CaO), 9.77. Found: C, 41.85; H, 4.85; N, 16.90; Ca, 6.93; Ash (CaO), 10.17.

The total yield of practically pure 5-CHO-THF was 1.49 g (33.5% from FA).

Fraction 3 gave a sample that was shown by HPLC to contain the following uv-absorbing components: p-aminobenzoylglutamic acid (<1%), 10-CHO-DHF (<5.5%), 10-CHO-FA (~1%), and 5-CHO-THF (~92.5% by difference).

The sample from fraction 4 showed (HPLC) the following components: p-aminobenzoylglutamic acid (<2%), 10-CHO-DHF (<20%), 10-CHO-FA (~1%), and 5-CHO-THF (~77% by difference).

In a large-scale synthesis, folic acid (600 g) was converted to the impure calcium salt of 5-CHO-THF via the catalytic hydrogenation of 10-CHO-FA over Pt in $CF_3CO_2H$. Four glass columns (8×120 cm) containing Florisil (2.6 kg) were prepared as described above. The 5-CHO-THF sample (465 g) was divided into 16 portions, and each portion (24–30 g) was eluted (rate, 3–5 ml/min) from one of the columns, each column being used four times. The development of a column was followed by determing the HPLC chromatogram of the eluate. During the first run, the 5-CHO-THF band appeared after a volume of 5 l. was collected. In later runs on the same column, a volume of 7.5 l. was collected before 5-CHO-THF started to elute. Each 5-CHO-THF fraction (~4.5 l.) was treated as described above. The combined samples were extracted with $O_2$-free $H_2O$ and filtered to remove an insoluble material. The filtrate was lyophilized to give the product: yield, 213 g (28% from FA). The HPLC chromatogram showed only trace amounts of p-aminobenzoylglutamic acid and Table 2

| Fraction | Flow rate ml/min | Collection time, hr | Volume, ml | Volume 25%$^a$ $CaCl_2$, ml | Sample wt, g | $80_{max}^{282}/\lambda_{min}^{242}$ |
|---|---|---|---|---|---|---|
| 1 | 0.6 | 6.5 | ~234 | 2 | 0.36 | 4.38 |
| 2 | 0.6 | 10 | ~360 | 3 | 1.2 | 4.62 |
| 3 | 3.0 | 8 | ~1,400 | 2 | 0.50 | 3.86 |
| 4 | 0.6 | 16 | ~576 }$^b$ | | | |
|  | 5.0 | 5 | ~1,500 | 4 | 0.18 | 2.84 |
|  |  |  |  | total | 2.24 (75% recovery) | |

$^a$After concentration of the fraction in vacuo.
$^b$Eluates combined.

Each fraction was concentrated to about 1/5 volume in vacuo (oil pump) at ~45° when an off-white flocculent solid began to precipitate. Each of the resulting mixtures was adjusted to pH 12 (meter) with 1 N NaOH and filtered through a thin Celite pad to remove the somewhat gelatinous insoluble material (MgO). The clear filtrates were adjusted to pH 7 (meter) with dilute HCl, treated with 25% aqueous $CaCl_2$ solution (clarified by filtration), readjusted to pH 7.5 (meter), and diluted slowly with 5 volumes of cold EtOH. The white precipitates were collected by filtration and dried in vacuo over $P_2O_5$.

10-CHO-DHF. $\lambda_{max}$, nm ($\epsilon \times 10^{-3}$): pH 7-287 (31.5); 0.1 N NaOH-282 (30.8). $\lambda_{max}{}^{282}/\lambda_{min}{}^{242} = 4.8$.

(C) Nonchromatographic Purification of Citrovorum Factor (1) The hygroscopic, brown, gummy residue (~400 g) containing glass-fiber filter pads obtained in the conversion of (5,10-CH-THF)+Cl− to 5-CHO-THF.Ca was stirred under N$_2$ in deaerated H$_2$O (4 l.), and the pH of the medium was adjusted to 7.5 with solid Ca(OH)$_2$ (~1 g). The glass fibers were removed by filtration, and the residue was washed with portions of deaerated H$_2$O (2 l.) until the washings were colorless. The clear filtrate was cooled in an ice bath and diluted with 0.1 volume of EtOH (600 ml). The precipitated dark hygroscopic yellow-brown solid was collected by filtration, washed with EtOH, and dried in vacuo over P$_2$O$_5$: yield, 199 g. $\lambda_{max}{}^{282}/\lambda_{min}{}^{242} = 3.7$ The filtrate was diluted with additional EtOH (total, 3 l.), and the precipitated pale yellow solid was collected by filtration, washed with EtOH and dried in vacuo over P$_2$O$_5$: yield, 17 g. $\lambda_{max}{}^{282}/\lambda_{min}{}^{242} = 3.90$.

The clear, yellow filtrate was diluted with additional EtOH (total, 15 l.); after cooling, the resulting cream-colored precipitate was collected by filtration, washed with EtOH, and dried in vacuo over P$_2$O$_5$: yield, 75 g. $\lambda_{max}{}^{282}/\lambda_{min}{}^{242}$ (0.1 N NaOH) = 4.19. HPLC assay of this sample indicated the presence of 5-CHO-THF.Ca (85%), PABGA.Ca (~2%), 10-CHO-DHF.Ca (~2%), 10-CHO-FA.CA (trace), and pterins (~1%). No doubt this sample also contained EtOH and H$_2$O (<10%).

(2) Additional experiments were carried out on portions of the large crop of impure 5-CHO-THF obtained as described under procedure (C-1) above.

A turbid solution of this material (3.00 g) in H$_2$O (100 ml) containing about an equimolar amount of MgCl$_2$.6H$_2$O (1 g) was treated portionwise with solid Ca(OH)$_2$.. The pH increased rapidly to ~10.5, then remained between 10.5–10.8. During this period a yellow-brown granular precipitate separated from the mixture after which the pH increased rapidly to 12 as more Ca(OH)$_2$ was added. After stirring for an additional 30 minutes, the solid was removed by filtration under N$_2$ pressure and dried in vacuo over P$_2$O$_5$: Yield, 1.40 g. The major portion of this residue is probably composed of CaO and MgO; however, the HPLC chromatogram showed the presence of a number of impurites and some 5-CHO-THF.

The clear filtrate was adjusted to pH 7.5 with dilute HCl followed by the dropwise addition of EtOH (~20 ml) until permanent turbidity was reached. This mixture was cooled to 10°, and the yellow solid was collected by filtration and dried in vacuo over P$_2$O$_5$: yield, 0.64 g. $\lambda_{max}{}^{282}/\lambda_{min}{}^{242} = 3.71$. The HPLC chromatogram showed that this sample contained only small amounts of the usual impurities, but increased amounts of FA and an unidentified material with a longer retention time. Apparently FA and the unidentified material were generated during the base treatment of this sample in the presence of MgCl$_2$. A magnesium analysis indicated the presence of a trace amount of magnesium (0.003%).

Anal. Calcd for C$_{20}$N$_{21}$N$_7$O$_7$.Ca.0.5C$_2$H$_6$O.1.2H$_2$O: C, 45.35; H, 4.78; N, 17.63; Ca, 7.21; Ash (CaO), 10.08. Found: C, 45.11; H, 5.01; N, 17.38; Ca, 7.20; Ash (CaO), 10.07.

The filtrate was diluted with three volumes of EtOH (300 ml), and the resulting mixture was cooled in an ice bath. The white solid was collected by filtration, washed with EtOH, and dried in vacuo over P$_2$O$_5$: yield, 1.33 g. $\lambda_{max}{}^{282}/\lambda_{min}{}^{242} = 4.78$. HPLC assay and elemental analysis indicated the presence of 5-CHO-THF. Ca (86%), PABGA.Ca (1%), 10-CHO-DHF (<1%), 10-CHO-FA (<1%), pterins (<1%), EtOH (4.2%), H$_2$O (3.3%), and unidentified material (~2.5%).

Anal. Calcd for C$_{20}$H$_{21}$N$_7$O$_7$.Ca.0.5C$_2$H$_6$O.H$_2$O: C, 45.65; H, 4.74; N, 17.75; Ca, 7.25; Ash (CaO), 10.14. Found: C, 45.59; H, 5.06; N, 17.69; Ca, 7.51; Ash (CaO), 10.51.

When the above experiment was repeated using twice the weight of MgCl$_2$, a smaller amount (0.77 g) of purified 5-CHO-THF was recovered.

It is thought that the invention and many of its attendant advantages will be understood from the foregoing description, and it will be apparent that various changes may be made in the methods as described herein without departing from the spirit and scope of the invention or sacrificing its material advantages, the forms hereinbefore described being merely the preferred embodiments thereof.

The embodiments of the invention in which an exclusive property or privilege is claimed are defined as follows:

1. A method for producing tetrahydrofolic acid from folic acid and isolating same, comprising the steps of:
    (a) reducing folic acid with sodium borohydride in alkaline aqueous solution employing an amount of said sodium borohydride at least equal to the weight of said folic acid to convert said folic acid to tetrahydrofolic acid;
    (b) adding acid to neutralize the reaction mixture so as to decompose any excess sodium borohydride;
    (c) dissolving ascorbic acid as an antioxidant in the reaction mixture;
    (d) acidifying the reaction mixture to a pH sufficient to precipitate said tetrahydrofolic acid; and
    (e) recovering said tetrahydrofolic acid from the reaction mixture.

* * * * *